United States Patent [19]

Henmi et al.

[11] 4,215,143
[45] Jul. 29, 1980

[54] ANTI-ULCER PHARMACEUTICAL COMPOSITION CONTAINING INOSITOL HEXASULFATE ALUMINUM OR SODIUM ALUMINUM SALT AS ACTIVE INGREDIENT

[75] Inventors: Zen-ichi Henmi, Mobara; Akira Kotaki, Tokyo; Takafumi Kitano, Mobara, all of Japan

[73] Assignee: Mitsui Toatsu Chemicals, Incorporated, Tokyo, Japan

[21] Appl. No.: 940,205

[22] Filed: Sep. 7, 1978

[30] Foreign Application Priority Data

Feb. 24, 1978 [JP] Japan ................................. 53-19770

[51] Int. Cl.² .......................................... A61K 31/185
[52] U.S. Cl. ...................................................... 424/315
[58] Field of Search ........................................ 424/315

[56] References Cited
PUBLICATIONS

Chem. Abstr. vol. 66, (1967), 79569m.
Chem. Abstr. vol. 67, (1967), 76305g.
Chem. Abstr., vol. 55, (1961), 3446–3447, (Takahashi et al).

Primary Examiner—Frederick E. Waddell

[57] ABSTRACT

Inositol hexasulfate aluminum and sodium aluminum salts have excellent anti-ulcer, antacid and antipeptic effects. Examination of the action of these compounds on various types of experimental gastric and duodenal ulcers in rats has shown that they have an excellent inhibitory effect on Shay's ulcer, acetic acid ulcer, stress ulcer, cysteamine duodenal ulcer, and aspirin ulcer. In addition, examination of the action of these compounds on the amount of gastric juice secreted, the acidity of gastric juice, and the activity of pepsin in rats has revealed their excellent antacid and antipeptic effects.

2 Claims, No Drawings

ANTI-ULCER PHARMACEUTICAL COMPOSITION CONTAINING INOSITOL HEXASULFATE ALUMINUM OR SODIUM ALUMINUM SALT AS ACTIVE INGREDIENT

BACKGROUND OF THE INVENTION

1. Field of the Invention

This invention relates to anti-ulcer pharmaceutical compositions and, more particularly, to such compositions containing inositol hexasulfate aluminum or sodium aluminum salt as an active ingredient.

2. Description of the Prior Art

Inositol hexasulfate is a well-known compound and may usually be prepared by condensing inositol and sulfuric acid with elimination of water. Its sodium salt can be obtained by adding the condensation product dropwise to an aqueous solution of a water-soluble sodium salt (selected from suitable halides, organic carboxylates, nitrate, etc. of sodium). Inositol hexasulfate aluminum salt can be obtained by mixing an aluminum chloride solution with an aqueous solution of the sodium salt prepared as above and then adding an aqueous sodium hydroxide solution until the mixture becomes weakly acidic. Further, inositol hexasulfate sodium aluminum salt can be obtained by passing an aqueous solution of the sodium salt through a column of acid type cation exchange resin and then mixing the resulting aqueous solution of free inositol hexasulfate with an aqueous sodium aluminate solution.

Although inositol hexasulfate aluminum and sodium aluminum salts are expected to have some biological effect or other, no reports have heretofore dealt with their pharmacological activity as well as their preparation.

On the other hand, it is well known that the sulfates of sugars have anti-ulcer effects. Nevertheless, there have been no reports about the action of inositol and its derivatives on peptic ulcer.

SUMMARY OF THE INVENTION

As a result of intensive research into the pharmacological activity of inositol hexasulfate aluminum and sodium aluminum salts, the present inventors have found that these compounds have excellent anti-ucler, antacid and antipeptic effects.

The term "inositol hexasulfate aluminum salt" as used herein denotes any of the compounds having the formula

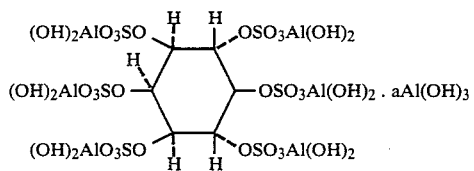

(I)

wherein a is an integer of from 0 to 6, and usually contains 6–12 molecules of water of crystallization. This salt is a white powder having no definite melting point and very slightly soluble in solvents such as water, absolute ethanol, benzene, etc. On drying at 80° C. for 4 hours under a reduced pressure of 1 mmHg, it loses the water of crystallation to give the anhydrous salt. Its infrared spectrum exhibits absorption peaks at $2.86\mu$ (OH groups in the water of crystallization), $6.13\mu$ (C-H bonds) and $8.00\mu$ (sulfuric ester groups).

An example of the preparation of inositol hexasulfate aluminum salt is given below.

A solution of 10.0 g of inositol hexasulfate sodium salt hexahydrate in 200 ml of water was mixed with a solution of 16 g of aluminum chloride hexahydrate in 100 ml of water. Then, the reaction mixture was adjusted to pH 4.0 by the addition of a 1 N aqueous sodium hydroxide solution. The resulting solution was stirred at room temperature for an hour. The precipitated crystals were separated by filtration, washed with 400 ml of water and then 400 ml of methanol, and dried to give 9.3 g of inositol hexasulfate aluminum salt. Its yield was 52.6%. The product did not melt at temperatures up to 230° C. Elemental analysis of the product showed that: C, 4.84 (5.00); H, 3.10 (2.95); S, 13.20 (13.35); Al, 18.55 (18.73). The values in parentheses are those calculated for $C_6H_6(OSO_3Al(OH)_2)_6 \cdot 4Al(OH)_3 \cdot 6H_2O$. The Al content was determined by atomic absorption spectroscopy.

The term "inositol hexasulfate sodium aluminum salt" as used herein denotes any of the compounds having the formula (I) wherein from 1 to 5 of the six $-OSO_3Al(OH)_2$ groups are replaced by an $-OSO_3Na$ group or groups, namely having the formula

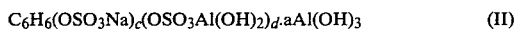

wherein a has the same meanings as defined for the formula (I), c is an integer of from 1 to 5, d is an integer of from 1 to 5, and the sum of (c+d) is equal to 6, and usually contains 6–12 molecules of water of crystallization. This salt is also a white powder having no definite melting point, partially soluble in water, and very slightly soluble in organic solvents such as absolute ethanol, benzene, etc. Like the aluminum salt, it loses the water of crystallization on drying at 80° C. under reduced pressure. The characteristic absorption peaks of its infrared spectrum lie at substantially the same wave numbers as for the aluminum salt.

An example of the preparation of inositol hexasulfate sodium aluminum salt is given below.

A column of acid type cation exchange resin was prepared by packing 45 ml of amberlite IR-120B (manufactured and sold by Rohm & Haas Co.) into a glass tube and passing therethrough 180 ml of 10% hydrochloric acid at a rate of 0.2–0.3 ml/sec. Then, the column was washed with about 300 ml of water until the Beilstein test of the washings became negative. Thereafter, a solution of 9.0 g of inositol hexasulfate sodium salt hexahydrate in 180 ml of water was passed through the column at a rate of 0.2–0.3 ml/sec. The solution was completely eluted with 80 ml of water. The whole eluate thus obtained was mixed with a solution of 2.46 g of sodium aluminate in 10 ml of water. The resulting solution was neutral. This solution was placed in an oil bath kept at about 40° C., evaporated to dryness under a reduced pressure of 15–17 mmHg, and further dried at 50° C. for 10 hours under a reduced pressure of 40 mmHg. The resulting solid was ground to give 9.1 g of a colorless powdery product. Its yield was 89.7%. Elemental analysis of the product showed: C, 6.96 (7.10); H, 2.47 (2.39); S, 18.63 (18.96); Al, 7.76 (7.98); Na, 6.94 (6.80). The values in parentheses are those calculated for $C_6H_6(OSO_3Al(OH)_2)_3 \cdot (OSO_3Na)_3 \cdot 6H_2O$. The Al content was determined by atomic absorption spectroscopy.

The anti-ulcer, antacid and antipeptic effects of these compounds, together with the acute toxicity thereof, were evaluated by a series of experiments. The inositol hexasulfate aluminum salt used in these experiments was the compound represented by the formula (I), wherein a=4 and contains 6 molecules of water of crystallization, and the inositol hexasulfate sodium aluminum salt used therein was the compound represented by the formula (II) wherein a=0, c=3, and d=3, and contains 6 molecules of water of crystallization.

(1) Anti-ulcer Effect

The anti-ulcer effect of some compounds of this invention was evaluated with regard to various types of experimental gastric and duodenal ulcers. The results obtained are given in Table 1. The method of evaluation for each type of ulcer is outlined below.

(i) Shay's Ulcer

Male rats of the Wistar strain, 7 or 8 weeks of age, were used in groups of ten. After 48 hours of fasting, the pyloric part of the stomach was ligated under ether anesthesia. Immediately after the operation, a certain amount of a compound to be tested was orally administered to each animal of a group. After 12 hours, the degree of ulceration occurring in the anterior part of the stomach was rated and regarded as an ulcer index (U.I.). Control rats were treated in the same manner as described above, except that they received no compounds to be tested. The results given in Table 1 are expressed in terms of the percentage of inhibition based on the U.I. obtained in the control group.

(ii) Stress Ulcer

Male rats of the Wistar strain, 8 weeks of age, were used in groups of ten. Each animal was immobilized in a stressing cage as developed by Takagi et al., immersed in water at 23° C. to the level of the xiphoid process, and thereby subjected to stress for 16 hours. Thereafter, the stomach was excised. The length of the ulcer formed in the glandular part of the stomach was measured and regarded as an ulcer index (U.I.). A certain amount of a compound to be tested was orally administered just before subjecting the animal to stress. The results are also expressed in terms of the percentage of inhibition based on the U.I. obtained in the control group receiving no compounds to be tested.

(iii) Aspirin Ulcer

Male rats of the Donryu strain, 10 or 11 weeks of age, were used in groups of ten. After 24 hours of fasting, a certain amount of a compound to be tested was orally administered to each animal of a group. Ten minutes later, aspirin was orally administered in a dose of 250 mg/kg. After 6 hours, the size of the ulcer formed in the glandular part of the stomach was rated by visual inspection and regarded as an ulcer index (U.I.). The results are also expressed in terms of the percentage of inhibition based on the U.I. obtained in the control group receiving no compounds to be tested.

(iv) Cysteamine Duodenal Ulcer

Male rats of the Donryu strain, 10 or 11 weeks of age, were used in groups of ten. After 24 hours of fasting, a certain amount of a compound to be tested was orally administered to each animal of a group. Thirty minutes later, cysteamine hydrochloride was orally administered in a dose of 400 mg/kg. After 18 hours, the product of the maximum and minimum diameters of the ulcer formed in the duodenum was determined and regarded as an ulcer index (U.I.). The results are also expressed in terms of the percentage of inhibition based on U.I. obtained in the control group receiving no compounds to be tested.

(v) Acetic Acid Ulcer

Male rats of the Wistar strain, 6 weeks of age, were used in groups of ten. Under ether anesthesia, each animal was laparotomized, a round frame (with an inside diameter of 5 mm) made of stainless steel was applied to the anterior wall of the stomach, and 100% acetic acid was poured into the frame. After 30 seconds, the acetic acid was removed and the abdomen was closed. Starting on the 7th day after the operation, a certain amount of a compound to be tested was orally administered twice a day to each animal of a group for a period of 7 days. Thereafter, the degree of healing of the ulcer was rated by visual insepction and regarded as an ulcer index (U.I.). The results are also expressed in terms of the percentage of healing based on the U.I. obtained in the control group receiving no compounds to be tested.

Table 1

Inhibitory or Healing Promotion Effect of Some Compounds of This Invention on Various Types of Experimental Ulcers

| Type of Ulcer | Aluminum Salt (mg/kg, p.o.) | | Sodium Aluminum Salt (mg/kg, p.o.) | |
|---|---|---|---|---|
| | 100 | 250 | 100 | 250 |
| Shay's Ulcer | 84 | 86 | 87 | 90 |
| Stress Ulcer | — | 32 | — | 30 |
| Aspirin Ulcer | 52 | 56 | 42 | 49 |
| Cysteamine Duodenal Ulcer | 43 | 38 | — | — |
| Acetic Acid Ulcer | 28 | 32 | 23 | 28 |

Notes:
1 "p.o." stands for "per os (= by mouth)".
2 The results of the former four experimental ulcers are expressed in terms of the percentage of inhibition, whereas the results of acetic acid ulcer are expressed in terms of the percentage of healing, and in every case greater values indicate better results.

(2) Effect on Gastric Juice Secretion, Gastric Juice Acidity and Pepsin Activity Male rats of the Donryu strain, 11 weeks of age, were used in groups of ten. After 24 hours of fasting, the pylorus was ligated. Four hours later, the gastric juice was collected and its volume was measured. Then, its acidity was determined by titrating an aliquot of the gastric juice with 0.05 N sodium hydroxide. Further, the activity of pepsin was determined by Anson's method. A definite amount (250 mg/kg) of a compound to be tested was orally administered immediately after the ligation of the pylorus. The results obtained are given in Table 2.

Table 2

Inhibitory Effect of Some Compounds of This Invention on Gastric Juice Secretion, Gastric Juice Acidity and Pepsin Activity

| Test Item | Control Group (solvent alone, p.o.) | Aluminum Salt-Treated Group (250 mg/kg, p.o.) | Sodium Aluminum Salt-Treated Group (250 mg/kg, p.o.) |
|---|---|---|---|
| Amount of Gastric Juice Secreted | 4.9 ± 0.4 | 3.6 ± 0.4* | 3.6 ± 0.4* |

Table 2-continued

Inhibitory Effect of Some Compounds of
This Invention on Gastric Juice Secretion,
Gastric Juice Acidity and Pepsin Activity

| Test Item | Control Group (solvent alone, p.o.) | Aluminum Salt-Treated Group (250 mg/kg, p.o.) | Sodium Aluminum Salt-Treated Group (250 mg/kg, p.o.) |
|---|---|---|---|
| (ml) |  |  |  |
| Acidity of Gastric Juice (mEq/l) | 92.5 ± 3.7 | 57.8 ± 12.9* | 61.1 ± 11.4* |
| Activity of Pepsin (mg/ml) | 7.4 ± 0.5 | 4.8 ± 0.4** | 5.1 ± 0.5** |

Notes:
1 "p.o." stands for "per os (= by mouth)".
2 *The difference between the treated and control groups was significant at the 5% level by T-test.
**The difference between the treated and control groups was significant at the 1% level by T-test.

(3) Acute Toxicity

Male and female mice of the dd Y strain, 4 weeks of age, as well as male and female rats of the Wistar strain, 7 weeks of age, were used in groups of ten. They were preliminarily raised for a week. Then, two compounds to be tested were dissolved or suspended in physiological saline and administered orally or subcutaneously. In the case of oral administration, the highest possible doses of 0.2 ml/10 g for mice and 2 ml/100 g for rats were used which both corresponded to 5,000 mg/kg. In the case of subcutaneous administration, the doses were reduced to ½. After the administration, the animals were observed for 7 days to detect the development of abnormalities. The animals that died during this period of observation were subjected to postmortem examination. The results obtained are given in Table 3.

Table 3

Acute Toxicity of Some Compounds of
This Invention in Mice and Rats

| Animal Species | LD$_{50}$ Values (mg/kg) of Aluminum and Sodium Aluminum Salts | |
|---|---|---|
|  | Subcutaneous | Oral |
| Mouse | >2,500 | >5,000 |
| Rat | >2,500 | >5,000 |

As can be seen from Table 3, the LD$_{50}$ values of the aluminum and sodium aluminum salts were almost equal to each other.

DESCRIPTION OF THE PREFERRED EMBODIMENTS

As is evident from the above-described experiments, the compounds of the present invention show excellent anti-ulcer effects and have utility in the field of pharmaceutical industry. In the treatment of adult patients with peptic ulcer, these compounds are preferably administered in a daily dose of from 500 to 3,000 mg, depending on the dosage form and the manner of division.

Like other gastrointestinal drugs, the compositions of this invention may be formed into oral preparations by any of conventional procedures. In order to exhibit their efficacy in the gastrointestinal tract, they may take a variety of dosage forms such as tablets, capsules, granules, dry syrups, solutions, etc., depending on the symptoms of the patient and other factors.

In the preparation of tablets which are a popular form for oral administration, inositol hexasulfate aluminum or sodium aluminum salt is mixed with an excipient for oral use comprising one or more diluents selected from lactose, starch, crystalline cellulose, calcium phosphate, calcium carboxymethylcellulose, etc., in the proportion of 10 parts by weight of active ingredient to 1-10 parts by weight of excipient. If desired, a binder such as gelatin, polyvinyl pyrrolidone, hydroxypropyl-cellulose, etc. is added in the form of a solution. The resulting mixture is granulated by conventional procedure and, after the addition of a lubricant such as calcium stearate, talc, silicic anhydride, etc., formed into tablets by means of a tableting machine. The tablets may further be sugar-coated or film-coated by conventional procedure.

In the preparation of granules, inositol hexasulfate aluminum or sodium aluminum salt is mixed with an excipient comprising one or more members selected from the above-enumerated diluents, sucrose, mannitol, etc., in the proportion of 10 parts by weight of active ingredient to 1-10 parts by weight of excipient. Then, a binder as described above is added in the form of a solution. The resulting mixture is granulated and dried by conventional procedure.

Two typical formulas for the preparation of tablets and granules are given below.

(1) Each tablet (280 mg) contains:
Active ingredient: 250 mg
Corn starch: 25 mg
Hydroxypropylcellulose: 2 mg
Calcium stearate: 3 mg (2) Each gram of granular preparation contains:
Active ingredient: 900 mg
Corn starch: 50 mg
Crystalline cellulose: 40 mg
Hydroxypropylcellulose: 10 mg In view of the gastrointestinal indications for the use of the compositions of this invention, their oral preparations are very likely to be combined with other active ingredients. In practice, they can be stably combined, for example, with other gastrointestinal drugs including various antacids such as dried aluminum hydroxide gel, magnesium aluminate metasilicate, magnesium silicate, etc.

What is claimed is:

1. An anti-ulcer pharmaceutical composition comprising as an active ingredient a therapeutically effective amount of a compound selected from the group consisting of inositol hexasulfate aluminum salt of the formula:

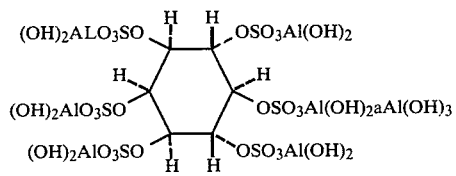

wherein "a" is an integer of from 0 to 6 and contains 6-12 molecules of water of crystallization and inositol hexasulfate sodium aluminum salt of the formula

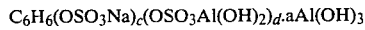

wherein "a" is an integer of from 0 to 6, "c" is an integer of from 1 to 5, "d" is an integer of from 1 to 5, and the sum (c+d) is equal to 6, the composition containing 6 to 12 molecules of water of crystallization and a pharmaceutically acceptable carrier.

2. An anti-ulcer pharmaceutical composition comprising as an active ingredient an amount of 10 parts by weight of a compound selected from the group consisting of inositol hexasulfate aluminum salt of the formula:

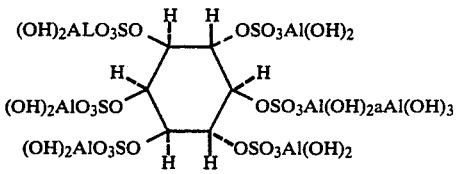

wherein "a" is an integer of from 0 to 6 and contains 6–12 molecules of water of crystallization and inositol hexasulfate sodium aluminum salt of the formula $$C_6H_6(OSO_3Na)_c(OSO_3Al(OH)_2)_d \cdot aAl(OH)_3$$

wherein "a" is an integer of from 0 to 6, "c" is an integer of from 1 to 5, "d" is an integer of from 1 to 5, and the sum (c+d) is equal to 6, the composition containing 6 to 12 molecules of water of crystallization per 1–10 parts by weight of a pharmaceutically acceptable carrier.

* * * * *